United States Patent [19]

Ghislaine et al.

[11] Patent Number: 4,823,804

[45] Date of Patent: Apr. 25, 1989

[54] APPARATUS FOR MONITORING ACTIVITY LEVEL OF HUMAN ORGAN

[75] Inventors: Marquis Ghislaine, Les Ulis; André Martin, Joue-Les-Tours; Jean Murat, Tours; Jean-Pierre Prulhiere, Bordeaux, all of France

[73] Assignees: Universite de Tours Francois Rabelais, Paris; Commissariat A L'Energie Atomique, Tours Cedex, both of France

[21] Appl. No.: 109,258

[22] Filed: Oct. 15, 1987

[30] Foreign Application Priority Data

Oct. 15, 1986 [FR] France ............... 86 14328

[51] Int. Cl.$^4$ .............................................. A61B 5/04
[52] U.S. Cl. ................................................ 128/733
[58] Field of Search ............... 128/773, 731, 710, 746, 128/732

[56] References Cited

U.S. PATENT DOCUMENTS

| | | | |
|---|---|---|---|
| 3,978,847 | 9/1976 | Fehmi et al. | 128/732 |
| 4,461,301 | 7/1984 | Ochs | 128/732 |
| 4,498,080 | 2/1985 | Culver | 128/732 |
| 4,705,049 | 11/1987 | John | 128/731 |

OTHER PUBLICATIONS

Morguet et al., "Microcomputer-Based Measurement . . . ", Med. Progr. Technol, 8, 77–82 (1981).
Rompelman, O. et al. "Measurement of Heart Rate . . . ", IEEE Transaction of Biomed Engineering, BME-29 503–510, No. 7, 1982.
Bellahsene et al. "An Improved Method for Recording . . . ", IEEE Transaction on Biomedical Engineering, BME-32, No. 11, 911–915 (1985).
Stevenage, G. B. et al., Medical and Biological Engineering 13 No. 2, pp. 266–271, Mar. 1985.

Primary Examiner—Francis Jaworski
Assistant Examiner—George Manuel
Attorney, Agent, or Firm—Michael N. Meller

[57] ABSTRACT

An apparatus for monitoring the activity level of an organ of the human body.

The apparatus processes digital values recorded in the memory of a processor. These digital values correspond to the analog values of a differential signal supplied after amplification and filtration of activity signals supplied by sensors. The memory contains a program for processing the digital values by sampling during each period of a succession of periods shifted by a predetermined time interval. The program controls the calculation of the Fourier transform of these values during each period. The frequency spectrum of the input signal is obtained during each interval. During each interval the processor detects the peak of the spectrum relative to the organ to be studied, as well as the amplitude maximum of that peak. The processor supplies a signal representing the evolution of the maxima of the peaks for all the time intervals. This signal is characteristic of the activity level of the organ to be studied.

4 Claims, 2 Drawing Sheets

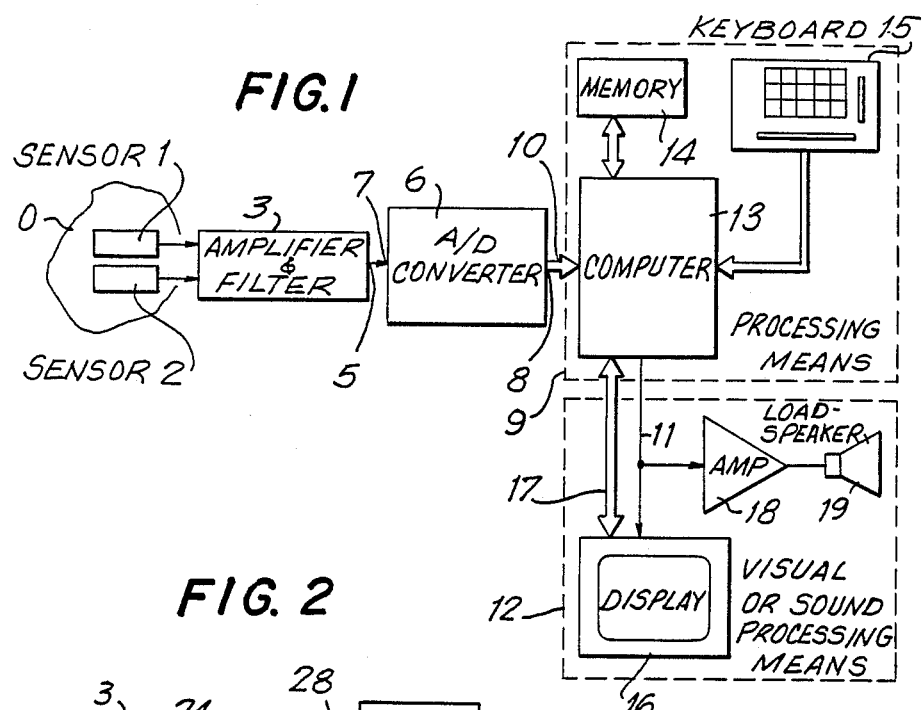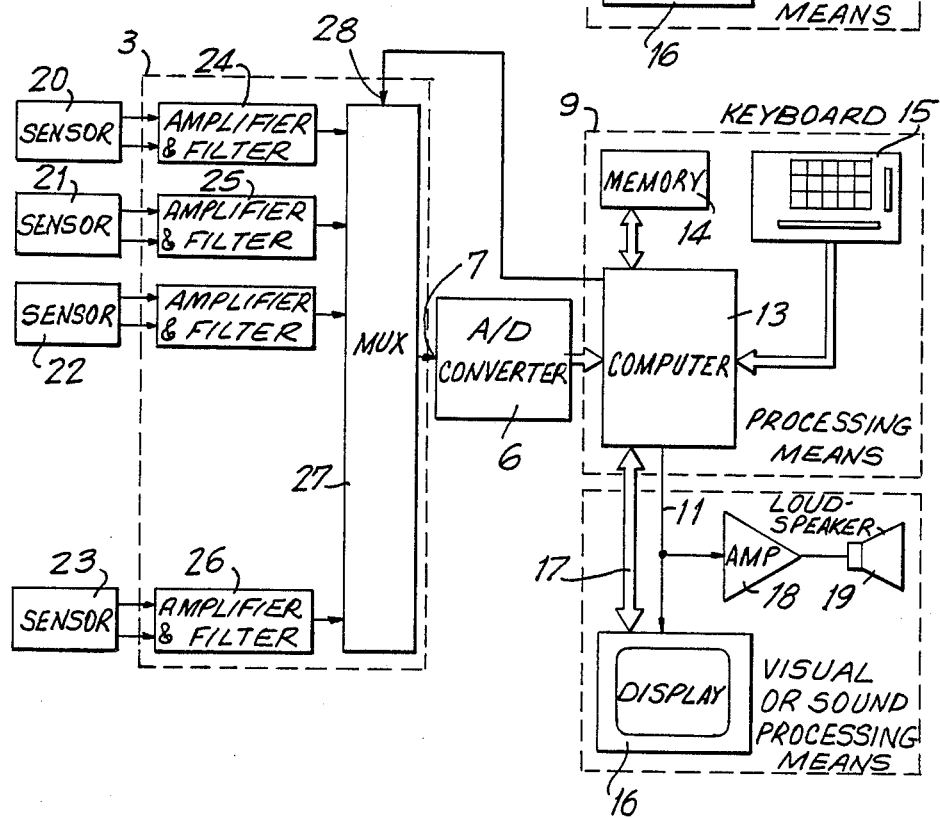

SPECIFIC FREQUENCY
BAND OF STUDIED ORGAN

APPARATUS FOR MONITORING ACTIVITY LEVEL OF HUMAN ORGAN

DESCRIPTION

The present invention relates to an apparatus for monitoring the activity level of an organ of the human body. It applies to the monitoring of the activity level of organs such as the stomach, intestines, etc. It enables a patient to voluntarily check the motricity of the studied organ by a counterreaction technique known as bioretroaction. It gives information on the activity level of an organ and enables a patient to control this level.

The digestive bioretroaction consists of a patient e.g. visually displaying a curve representative of the gastric activity. The patient can then check this activity by muscular contraction or decontraction, or by a greater or lesser physical relaxation. The visual display of a curve representing this activity, particularly the gastric activity, is very difficult because it only evolves in the range of very low frequencies (below 0.2 Hz).

At present there is no high performance apparatus making it possible to effect, in real time, a bioretroaction for organs, whose activity is in the very low frequency range and in particular the digestive bioretroaction.

The presently known apparatuses making it possible to effect, in particular, digestive bioretroactions do not have high performance characteristics and lead to traumatisms for the patient. Thus, the apparatuses measuring e.g. the digestive rates use gastric or colic probes, cuff probes, microballoon probes, etc., which are introduced into the patient's stomach, which leads to unpleasantness for the patient and causes a modification and disturbance to the gastric or colic motricity, so that the bioretroaction is not very significant.

The known apparatuses making it possible to monitor the activity of an organ of the human body, but which do not make it possible to effect, in particular, a digestive bioretroaction, generally have two sensors positioned in the vicinity of the organ to be monitored. These sensors supply on an output a differential electric signal representative of the activity of said organ. The known apparatus also comprises amplification and filtration means connected by one input to the sensor output. These amplification and filtration means supply an amplified and filtered signal of the input signal on an output. This signal is supplied to an analog-digital converter, which supplies on an output digital values representative of the amplified and filtered analog signal. These digital values are applied to processing means supplying on an output signal characteristic of the activity of the organ. For example, visual processing means receive said characteristic signal, so that the patient can check or control the organ studied by bioretroaction. These known monitoring apparatuses can only be used for organs whose activity (rate) is represented by medium or low frequency signals, but not by very low frequency signals (case of the gastric system).

The invention aims at obviating the disadvantages and in particular at providing an apparatus for monitoring the activity of an organ of the human body, enabling a patient to check the activity of said organ by bioretroaction, said activity evolving in the very low frequency range.

The invention relates to an apparatus for monitoring the activity of an organ of the human body, having at least one pair of differential-connected sensors positioned in the vicinity of the organ to be monitored and supplying on their respective outputs differential electric signals representative of the activity of said organ, amplification and filtration means connected by respective inputs to the outputs of the sensors and supplying on one output an amplified and filtered differential signal of the input signals, an analog-digital converter connected by an input to the output of the amplification and filtration means for supplying on an output digital values corresponding to the amplified and filtered input analog signal, processing means connected by an input to the output of the converter for processing the digital values and for supplying on at least one output a signal characteristic of the activity level of the organ, and means for the visual and/or sound processing of said characteristic signal, connected to the output of the processing means, characterized in that the processing means comprise a processor having an input and an output, storage means connected to the processor for recording said digital values to be processed and for recording a program for processing said digital values by sampling corresponding to each period of a succession of predetermined periods, the start of a period being shifted by a predetermined time interval relative to the start of the preceding period of said succession, the processing program calculating the Fourier transform of these digital values on each period to obtain in each predetermined time interval, the frequency spectrum of the input signal, said programme then controlling, for each spectrum, the selection of the peak of the spectrum corresponding to the organ to be studied and the detection of the amplitude maximum of said peak, the processing means supplying on their output a signal representing the evolution of the amplitude maxima of the peaks of the spectra corresponding to the successive time intervals, said signal being characteristic of the activity level of the organ.

According to another feature, the visual processing or working means are constituted by a display means and/or a printer connected to the output of the processing means.

According to another feature, the sound processing or working means incorporate an amplifier connected to the output of the processing means and a loudspeaker connected to an output of said amplifier for supplying sounds, whose tonality is dependent on the evolution of the characteristic signal.

According to an embodiment of the apparatus according to the invention, the latter comprises a plurality of sensors positioned in the vicinity of the organ, the amplification and filtering means having for each sensor an amplification and filtering channel, whereof one input is connected to the output of the corresponding sensor, said amplifying and filtering channel supplying on an output an amplified and filtered signal of the input signal, and an analog multiplexer having inputs respectively connected to the outputs of the amplifying and filtering channels and an input connected to a multiplexing control output of the computer, an output of said multiplexer being connected to the input of the analog-digital converter.

The features and advantages of the invention can be better gathered from the following description relative to the drawings, wherein:

FIG. 1 is a diagrammatic depiction of an embodiment of the apparatus according to the invention.

FIG. 2 is a diagrammatic depiction of another embodiment of the apparatus according to the invention.

Figure 3A:
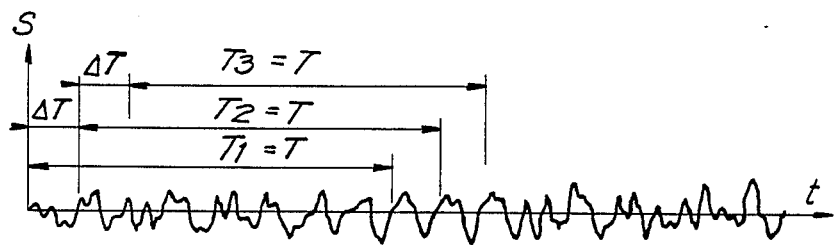
FIG. 3A is a timing diagram of the analog signal supplied by a sensor used in the apparatus according to the invention.

In the embodiment diagrammatically shown in FIG. 1, the apparatus according to the invention comprises a pair of differential-connected sensors 1, 2, positioned in the vicinity of the organ O to be monitored and supplying, on their respective outputs, differential analog electric signals representative of the activity level of said organ. These sensors are not described in detail here, because they are well known in the art and can e.g. be constituted by a sensor of the type used in the study of the heart rate.

The apparatus also comprises differential amplification and filtration means 3 connected by their respective inputs to the outputs of the sensors. These amplification and filtration means supply on an output 5 an amplified and filtered signal of the differential input signals.

An analog-digital converter 6 is connected by an input 7 to the output 5 of the amplification and filtration means 3. On an output 8, said converter supplies digital values corresponding to the amplified and filtered analog signal.

The apparatus also comprises processing means 9 connected by an input 10 to the converter output 8, for processing the digital values received and for supplying on at least one output 11, a signal characteristic of the activity level of the studied organ.

Finally, the apparatus comprises visual and/or sound processing means 12 for said characteristic signal which are connected to the output 11 of processing means 9 for receiving the characteristic signal.

The processing means 9 comprise a computer 13, whereof an input and an output respectively constitute the input 10 and output 11 of the processing means. These processing means also comprise storage means 14, connected to processor 13, for recording the digital values to be processed and for recording the values resulting from said processing, as well as for recording a program for processing said digital values and which will be described in greater detail hereinafter.

The storage means 14 can e.g. be constituted by one or more programmable read only memories of the PROM or EPROM type, which make it possible to record the processing program, as well as at least one random access memory making it possible to record the digital values to be processed, as well as the values resulting therefrom. The processing means can also comprise a control keyboard 15.

The processing program stored in the storage means 14 of processor 13 makes it possible to sample the digital values supplied by converter 6, in accordance with the periods of a succession of predetermined periods. In this succession, the start of a period is displaced by a predetermined time interval relative to the start of the preceding period of said succession, as will be shown in greater detail hereinafter.

On each of these periods, the processing program also makes it possible to carry out a Fourier processing of the digital values. Thus, for each predetermined time interval the Fourier spectrum of the frequencies of the input signal for the elapsed period is obtained. This program then controls the search for the amplitude maximum of the frequency peaks of the Fourier spectrum for each time interval. The processing means supply on their outputs a signal representing the evolution of the amplitude maximum of the peaks of the spectra corresponding to the successive time intervals, said signal being characteristic of the activity level of the organ, as will be shown hereinafter.

No description will be given here of the sampling program of the input signal or the Program for Fourier processing and seeking the amplitude maxima, because these various programs are known in the art.

The visual or sound processing means 12 can comprise a display means 16 and/or a printer connected to the output 11 of processing means 9. Connection 17 e.g. permits an exchange of control signals between processing means 9 and the display means, or between the latter and the control keyboard 15, via processing means 9.

The processing means 12 can also comprise an amplifier 18 connected to the output 11 of the processing means and a loudspeaker 19 connected to an output of said amplifier for supplying sounds, whose tonality is dependent on the evolution of the characteristic signal of the activity of the studied organ.

On the screen of display means 16 appears a curve C representing the evolution of the activity of the studied organ as a function of time. Loudspeaker 19 supplies a sound, whose tonality varies as a function of the evolution of the activity of the studied organ.

FIG. 2 diagrammatically shows another embodiment of the apparatus according to the invention. The same means carry the same references in FIG. 2 as in FIG. 1. In this embodiment, the apparatus comprises a plurality of pairs of sensors 20, 21, 22, 23 of the aforementioned type. These sensors are positioned in the vicinity of the organ. For each sensor, the amplification and filtration means 3 comprise an amplification and filtration channel, an input of which is connected to the output of the pair of corresponding sensors. Each amplification and filtration channel supplies on an output an amplified and filtered signal of the differential input signals. The different amplification and filtration channels are represented at 24, 25, 26 in FIG. 2. The amplification and filtration means also incorporate an analog multiplexer 27 connected to the outputs of the amplification and filtration channels. This multiplexer comprises a control input 28 connected to a control output of computer 13 for receiving a multiplexing control signal obtained as a result of a clock within the computer and which is not shown in the drawing. An output of this multiplexer is connected to the input 7 of the analog-digital converter 6.

As in the preceding embodiment, the processing means 9 may incorporate the computer 13 and the storage means 14, as well as the control keyboard 15. The visual or sound processing means also incorporate, as hereinbefore, a display means 16 and/or an amplifier 18 connected to a loudspeaker 19.

In this embodiment, the apparatus makes it possible to select the most significant signals supplied by one or more sensors, so as to carry out a very precise monitoring of the activity level of the studied organ.

Figure 3B:
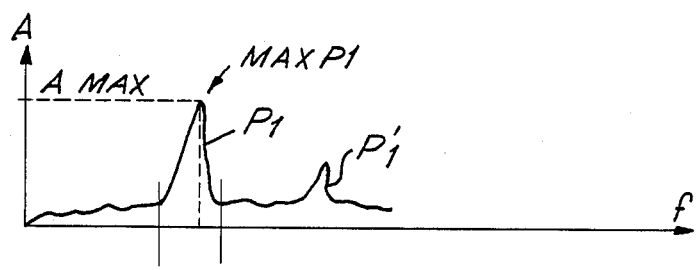
FIG. 3B shows the Fourier spectrum of the frequencies of the analog signal of FIG. 3A for a sampling period of said signal.
Figure 3C:
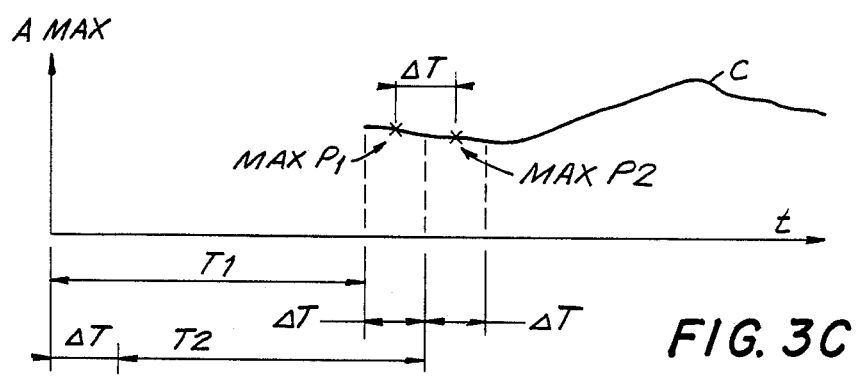
FIG. 3C is a timing diagram representing the evolution of the maxima of the peaks of the Fourier spectrum during the time of the analog signal supplied by the sensor, when said signal undergoes a Fourier processing, by successive equal periods shifted by a predetermined time interval.

FIGS. 3A, 3B and 3C provide a better understanding of the operation of the apparatus according to the invention.

The timing diagram of FIG. 3A shows the amplitude variations S, as a function of time t, of the output signal of one of the sensors of the apparatus. According to the invention, this signal is applied to an analog-digital converter and the digital values obtained are sampled during periods of a succession of predetermined periods of duration T. In FIG. 3A the first of said sampling periods is represented by T1=T.

According to the invention, the start of the second sampling period T2 of the same duration T is shifted with respect to the start of the preceding period T1 by a predetermined time interval $\Delta T$. In the same way, the start of the third sampling period T3 of duration T is displaced with respect to the start of the preceding period T2 by the predetermined time interval $\Delta T$. Thus, the storage means 14 of computer 13 record the digital values corresponding to these different shifted sampling periods, provided by the output of the analog-digital converter 6.

Then, in real time and for digital values corresponding to each of these periods, there is a Fourier processing in such a way as to obtain the frequency spectrum of the input signal for each period. This frequency spectrum for one of the considered periods is shown in exemplified manner in FIG. 3B (amplitude A of the spectrum as a function of frequencies f). This spectrum can have several peaks such as P1 and P'1. Within the spectrum A is selected the peak relative to the activity level of the studied organ by choosing the peak P1 located in the specific frequency band of the studied organ, whereas peak P'1, which generally has a lower amplitude, relates to the activity of another organ. In this way a succession of frequency spectra is obtained, calculated during periods T which are shifted relative to one another by a time interval $\Delta T$. Thus, the Fourier spectrum calculated during period T1 is obtained at the end of this period during the following time interval $\Delta T$. The processing means make it possible to only retain in the spectrum relative to each period the maximum amplitude of the peak, such as P1. The values of these maximum amplitudes, for the spectra corresponding to each sampling period, are obviously recorded in the storage means.

FIG. 3C is a timing diagram which represents as a function of time t, the evolution of the amplitude maximum $A_{max}$ of successive peaks P1 for different sampling periods. This evolution is represented by curve C, which corresponds to the characteristic signal supplied on the output 11 of computer 13. This signal is applied either to the display means 16, for allowing curve C to appear on the screen of said display means, or at the input of amplifier 18, so that loudspeaker 19 supplies a variable tonality sound corresponding to said curve.

The start of curve C can only appear at the end of the first sampling period, because the computer 13, during said period, processes the digital values corresponding to the sampling of the signal during said period. The corresponding Fourier spectrum can thus only be obtained during the time interval $\Delta T$ starting at the end of said first period T1. Thus, FIG. 3C shows in exemplified manner the maximum amplitude peak P1 obtained by the Fourier processing of the digital values corresponding to the sampling of the signal during the first period T1. In the same way, at P2 is shown the peak of the Fourier spectrum of maximum amplitude obtained by the Fourier processing of digital values corresponding to the sampling of the signal during period T2. This spectrum can only be obtained at the end of period T2, during the time interval $\Delta T$ following the end of period T2. Thus, curve C is the envelope of the maxima of the peaks of the Fourier spectra for successive periods.

The patient listening to the sound signal emitted by loudspeaker 19, or who sees the curve C appearing on the screen of the display means 16 can check the activity level of the studied organ by muscular contraction or decontraction or by modifying his physical state. The apparatus described hereinbefore permits a reaction of the patient in real time, without the latter being inconvenienced by internal probes. This apparatus consequently makes it possible for the patient to perform a bioretroaction, particularly for the checking his own stomach activity level.

We claim:

1. Apparatus for monitoring an activity level of an organ of a human body, comprising at least one pair of differentially connected sensors adapted to be positioned in the vicinity of said organ, said sensors supplying, on their respective outputs, electric signals representative of the activity level of said organ, differential amplification and filtering means respectively connected by inputs to the outputs of said sensors, said amplification and filtering means supplying on an output an amplified and filtered signal of the said electrical signals, an analog-digital converter connected by an input to the output of the amplification and filtering means, said analog-digital converter supplying on an output digital values corresponding to the amplitude of the amplified and filtered input analog signal, processing means connected by an input to the output of the converter, said processing means processing the digital values and supplying on at least one output a signal characterizing the activity level of said organ and visual and/or sound processing means of said characteristic signal connected to the output of said processing means, wherein said processing means comprise a processor, an input and output of which respectively constitute the input and the output of said processing means, storage means connected to said processor for recording said digital values to be processed and for recording a program for processing said digital values by a sampling corresponding to each period of a succession of periods of predetermined duration, the start of a period being shifted by a predetermined time interval compared with the start of the preceding period of said succession, the processing program controlling the calculation of the Fourier transform of said digital values during each period by the processor in order to obtain in each predetermined time interval, the frequency spectrum of the input signal, said program then controlling, for each spectrum, the selection of a peak maximum amplitude with corresponding to said organ for each spectrum and the detection of the amplitude of said peak of maximum amplitude, the processing means supplying on their output a signal representative of the evolution of the amplitude of said peaks of the maximum amplitude corresponding to the successive time intervals, said signal characterizing the activity level of said organ.

2. Apparatus according to claim 1, wherein the visual processing means comprise a visual display means and/or a printer connected to the output of the processing means.

3. Apparatus according to claim 1, wherein the sound processing means comprise an amplifier connected to the output said processing means and a loudspeaker connected to the output of said amplifier for supplying sounds whose tonality depends on the amplitude of the characteristic signal.

4. Apparatus according to claim 1, further comprising a plurality of sensors located in the vicinity of said organ, said amplification and filtering means having for each sensor an amplification and filtering channel, an input of which is connected to the output of the corresponding sensor, each of said amplification and filtering channels supplying on an output an amplified and filtered signal of the input signal, and an analog multiplexer having inputs respectively connected to the outputs of said amplification and filtering channels and an input connected to a multiplexing control output of said processor, an output of said multiplexer being connected to the input of said analog-digital converter.

* * * * *

UNITED STATES PATENT AND TRADEMARK OFFICE
CERTIFICATE OF CORRECTION

PATENT NO. : 4,823,804

DATED : April 25, 1989

INVENTOR(S) : Ghislaine Marquis et al.

It is certified that error appears in the above-identified patent and that said Letters Patent is hereby corrected as shown below:

ON THE TITLE PAGE, Item [19], "Ghislaine et al." should read

-- Marquis et al. --.

Item [75], "Marquis Ghislaine" should read

-- Ghislaine Marquis --.

Signed and Sealed this

Second Day of January, 1990

Attest:

JEFFREY M. SAMUELS

Attesting Officer  Acting Commissioner of Patents and Trademarks